United States Patent
Deblois et al.

(10) Patent No.: US 11,864,752 B2
(45) Date of Patent: Jan. 9, 2024

(54) ENDOSCOPIC STITCHING DEVICE FOR SUPPORTING SUTURE NEEDLES IN VARIOUS ORIENTATIONS

(71) Applicant: Covidien LP, Mansfield, MA (US)

(72) Inventors: Asa G. Deblois, New Haven, CT (US); Jonathan D. Thomas, New Haven, CT (US)

(73) Assignee: Covidien LP, Mansfield, MA (US)

( * ) Notice: Subject to any disclaimer, the term of this patent is extended or adjusted under 35 U.S.C. 154(b) by 158 days.

(21) Appl. No.: 17/462,770

(22) Filed: Aug. 31, 2021

(65) Prior Publication Data
US 2022/0160347 A1 May 26, 2022

Related U.S. Application Data

(60) Provisional application No. 63/116,580, filed on Nov. 20, 2020.

(51) Int. Cl.
*A61B 17/062* (2006.01)
*A61B 17/04* (2006.01)

(52) U.S. Cl.
CPC ...... *A61B 17/0469* (2013.01); *A61B 17/0625* (2013.01)

(58) Field of Classification Search
CPC ............ A61B 17/0469; A61B 17/0625; A61B 17/062; A61B 17/06061; A61B 17/0482; A61B 17/0483; A61B 17/0491; A61B 17/28; A61B 17/29; A61B 17/04
See application file for complete search history.

(56) References Cited

U.S. PATENT DOCUMENTS

| | | | |
|---|---|---|---|
| 2,363,334 A | 11/1944 | Jones | |
| 5,364,409 A * | 11/1994 | Kuwabara | A61B 17/0483 606/205 |
| 5,759,188 A | 6/1998 | Yoon | |
| 5,897,563 A | 4/1999 | Yoon et al. | |
| 5,993,466 A | 11/1999 | Yoon | |
| 6,126,665 A | 10/2000 | Yoon | |
| 6,171,316 B1 | 1/2001 | Kovac et al. | |
| 8,906,043 B2 | 12/2014 | Woodard, Jr. et al. | |
| 9,125,646 B2 | 9/2015 | Woodard, Jr. et al. | |
| 9,277,916 B2 | 3/2016 | Martin et al. | |
| 9,427,226 B2 | 8/2016 | Martin et al. | |
| 9,451,946 B2 | 9/2016 | Woodard, Jr. et al. | |

(Continued)

FOREIGN PATENT DOCUMENTS

SE 542609 C2 6/2020

OTHER PUBLICATIONS

International Search Report and Written Opinion of the International Searching Authority issued in corresponding application PCT/US2021/058889 dated Mar. 17, 2022 (15 pages).

*Primary Examiner* — Kathleen S Holwerda
*Assistant Examiner* — Daniel Icet
(74) *Attorney, Agent, or Firm* — Carter, DeLuca & Farrell LLP

(57) ABSTRACT

A surgical stitching device is configured for single hand operation that enables passage of a suture needle through tissue with minimal operational requirement. The surgical needle is selectively securable to a tool assembly of the surgical stitching device. The tool assembly includes a jaw configured to securely support various surgical needles in various orientations.

19 Claims, 11 Drawing Sheets

(56) References Cited

U.S. PATENT DOCUMENTS

| | | |
|---|---|---|
| 9,585,655 B2 | 3/2017 | Woodard, Jr. et al. |
| 9,814,457 B2 | 11/2017 | Martin et al. |
| 9,913,639 B2 | 3/2018 | Woodard, Jr. |
| 2008/0097482 A1* | 4/2008 | Bain .................. A61B 17/0625 606/144 |
| 2014/0128890 A1* | 5/2014 | Kappel .............. A61B 17/0469 606/147 |
| 2016/0030036 A1 | 2/2016 | Belman et al. |
| 2018/0221011 A1* | 8/2018 | Malkowski ...... A61B 17/06166 |
| 2020/0046341 A1 | 2/2020 | Skinlo et al. |

* cited by examiner

ENDOSCOPIC STITCHING DEVICE FOR SUPPORTING SUTURE NEEDLES IN VARIOUS ORIENTATIONS

CROSS-REFERENCE TO RELATED APPLICATIONS

This application claims the benefit of and priority to U.S. Provisional Patent Application No. 63/116,580, filed Nov. 20, 2020, the entire contents of which is incorporated by reference herein.

TECHNICAL FIELD

The disclosure relates to surgical devices for suturing or stitching and, more particularly, to an endoscopic suturing or stitching device including a jaw configured to support various suture needles thereto in various orientations.

BACKGROUND

One of the advances in recent years to reduce the invasiveness of surgical procedures is endoscopic surgery. Generally, endoscopic surgery involves incising through body walls. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the navel incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas.

In many surgical procedures, including those involved in endoscopic surgery, it is often necessary to suture bodily organs or tissue. In such surgical procedures, it is necessary to manipulate a suture needle, having a length of suture material attached thereto, with a surgical stitching device.

SUMMARY

The disclosure describes a surgical stitching device that demonstrates a practical approach to meeting the performance requirements and overcoming usability challenges associated with suturing intracorporeally.

In accordance with this disclosure, a surgical stitching device includes an arcuate suture needle, a handle assembly, an elongate shaft assembly extending distally from the handle assembly, and a tool assembly. The handle assembly includes a housing, a pair of handles, and an axial rod slidably supported in the housing. The axial rod is operatively coupled to the pair of handles such that actuation of the pair of handles cause axial displacement of the axial rod. The elongate shaft assembly includes an actuation rod operatively coupled to the axial rod for reciprocating displacement in an opposite direction, and an outer tube defining a lumen therethrough. The axial rod is slidably disposed in the lumen of the outer tube. The tool assembly includes a jaw coupled to the actuation rod. The jaw includes a recessed portion configured to engage a portion of the arcuate suture needle. The jaw is transitionable between a retracted configuration, in which, the recessed portion is in a proximal position to clamp the arcuate suture needle against the elongate shaft assembly and an advanced configuration, in which, the recessed portion is spaced apart from the elongate shaft assembly. The recessed portion has a first arcuate surface, a first planar surface proximal of the first arcuate surface, a second arcuate surface proximal of the first planar surface, and a second planar surface proximal of the second arcuate surface. The first arcuate surface has a first radius of curvature, and the second arcuate surface has a second radius of curvature different from the first radius of curvature.

In an aspect, the arcuate suture needle may have an arcuate portion having a radius of curvature identical to the first radius of curvature of the first arcuate surface of the recessed portion of the jaw.

In another aspect, an arcuate portion of the arcuate suture needle may have a radius of curvature identical to the second radius of curvature of the second arcuate surface of the recessed portion of the jaw.

In yet another aspect, the first planar surface may be coterminous with the first arcuate surface of the recessed portion of the jaw.

In still yet another aspect, the second planar surface may be coterminous with the second arcuate surface of the recessed portion of the jaw.

In an aspect, the recessed portion of the jaw may further include a third arcuate portion proximal of the second planar surface.

In another aspect, the third arcuate portion of the recessed portion of the jaw may have a third radius of curvature different from the first or the second radii of curvature.

In yet another aspect, the third arcuate portion may be coterminous with the second planar surface of the recessed portion of the jaw.

In still yet another aspect, the elongate shaft assembly may further include an inner tube secured to a distal end portion of the outer tube. The inner tube may define a second lumen dimensioned to slidably receive the actuation rod therethrough.

In an aspect, the inner tube may further include a lip extending radially inward.

In another aspect, the lip may have a recessed portion configured to engage a portion of the arcuate suture needle.

In yet another aspect, the recessed portion of the lip may have a radius of curvature identical to the radius of curvature of the arcuate portion of the arcuate suture needle.

In an aspect, the arcuate suture needle may have a penetrating end portion and a blunt end portion.

In another aspect, the jaw may define a cutout in communication with the recessed portion. The cutout may be configured to receive a portion of the arcuate suture needle therein.

In accordance with another aspect of the disclosure, a surgical stitching device includes an elongate shaft assembly including a tube having a lip extending radially inward and a jaw being movable relative to the tube to clamp an arcuate suture needle therebetween. The jaw includes a recessed portion including a first arcuate surface, a first planar surface proximal of the first arcuate surface, a second arcuate surface proximal of the first planar surface, and a second planar surface proximal of the second arcuate surface. The first arcuate surface has a first radius of curvature, and the second arcuate surface has a second radius of curvature different from the first radius of curvature.

In an aspect, the recessed portion of the jaw may further include a third arcuate surface proximal of the second planar surface.

In another aspect, the lip of the tube may define a recess having a radius of curvature identical to the second radius of curvature of the second arcuate surface of the recessed portion of the jaw.

In yet another aspect, the first planar surface may be coterminous with the first arcuate surface and the second arcuate surface.

In still yet another aspect, the surgical stitching device may further include a suture needle having a blunt end portion and a penetrating portion that diametrically oppose each other.

In still yet another aspect, the jaw may further define a cutout configured to receive a portion of the suture needle therein, the cutout may be in communication with the recessed portion of the jaw.

BRIEF DESCRIPTION OF DRAWINGS

The above and other aspects and features of this disclosure will become more apparent in view of the following detailed description when taken in conjunction with the accompanying drawings wherein like reference numerals identify similar or identical elements.

DETAILED DESCRIPTION

Figure 1:
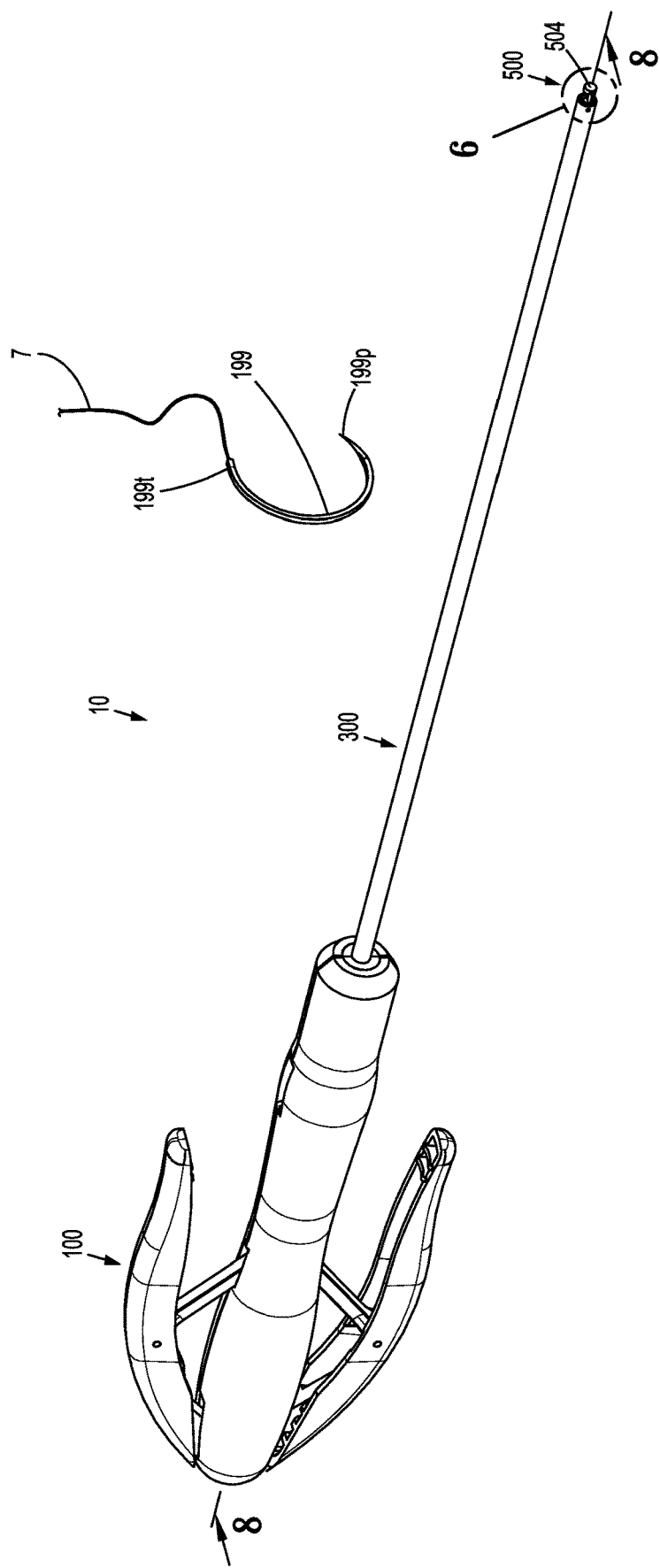
FIG. 1 is a perspective view of a surgical stitching device in accordance with the disclosure.

The surgical stitching device disclosed herein is described in detail with reference to the drawings, in which like reference numerals designate identical or corresponding elements in each of the several views.

As used herein, the term "distal" refers to the portion that is being described which is farther from a user, while the term "proximal" refers to the portion that is being described which is closer to a user. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

In FIG. 1, an exemplary surgical stitching device in accordance with the disclosure is shown generally as 10. The surgical stitching device 10 is adapted to be particularly useful in endoscopic or laparoscopic procedures. For example, the surgical stitching device 10 may be utilized in ventral hernia procedures. An endoscopic portion of the surgical stitching device 10 such as, e.g., a tool assembly 500, is insertable into an operative site, via a cannula assembly or the like. The surgical stitching device 10 includes a suture needle 199 that is supported on a jaw 504 of the tool assembly 500. The surgical stitching device 10 is configured for single hand operation that enables passage of the suture needle 199 through tissue with minimal operational requirements. The suture needle 199 has a round configuration such that a blunt end portion 199$t$ and a penetrating end portion 199$p$ diametrically oppose each other. A surgical suture 7 is attached to, e.g., the blunt end portion 199$t$ of the suture needle 199. The surgical stitching device 10 includes a handle assembly 100, an elongate shaft assembly 300 extending distally from the handle assembly 100, and the tool assembly 500 operatively supported on a distal end of the elongate shaft assembly 300.

Figure 2:
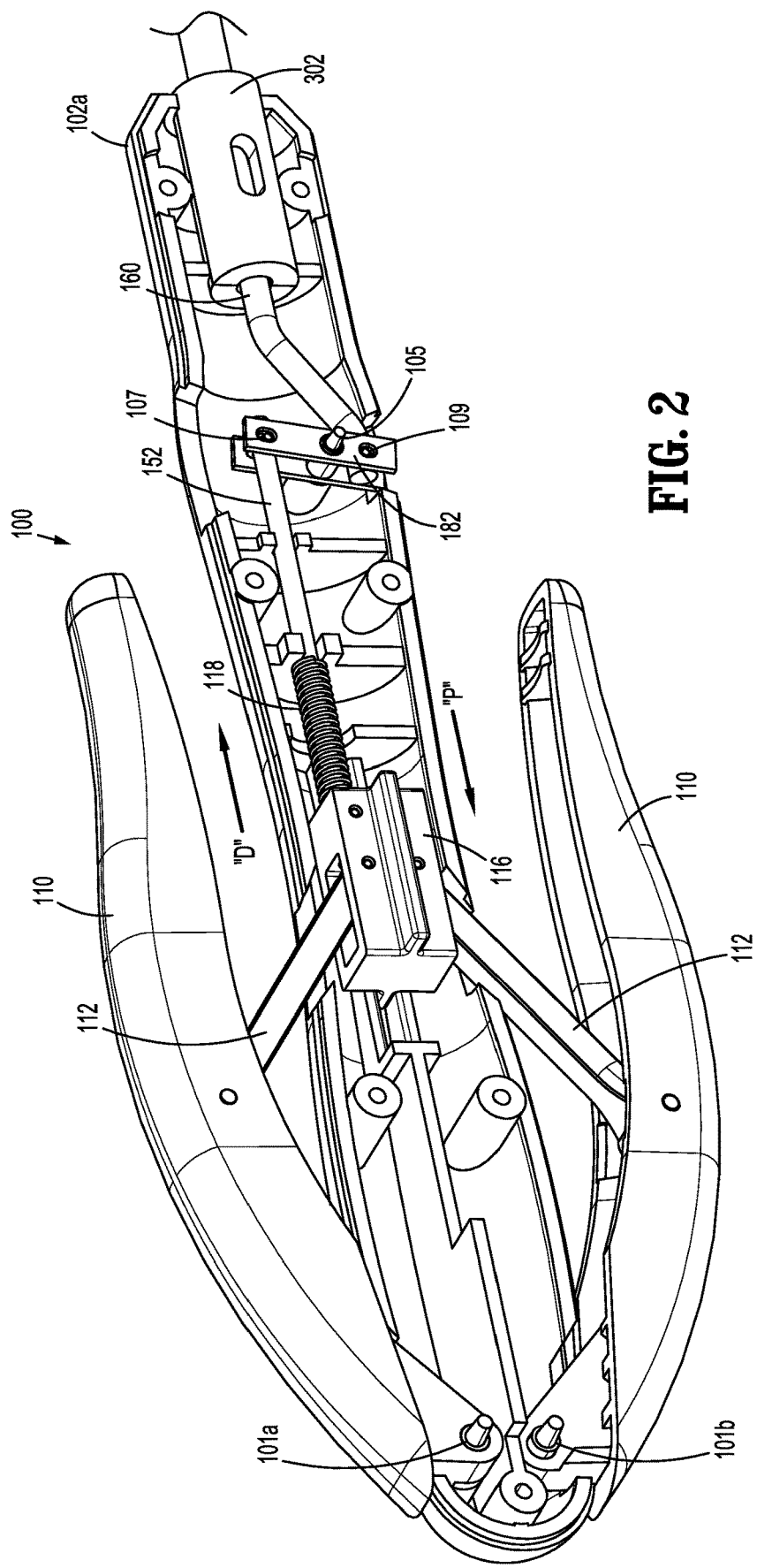
FIG. 2 is a perspective view of a handle assembly of the surgical stitching device of FIG. 1 with a first half of a housing removed.
Figure 3:
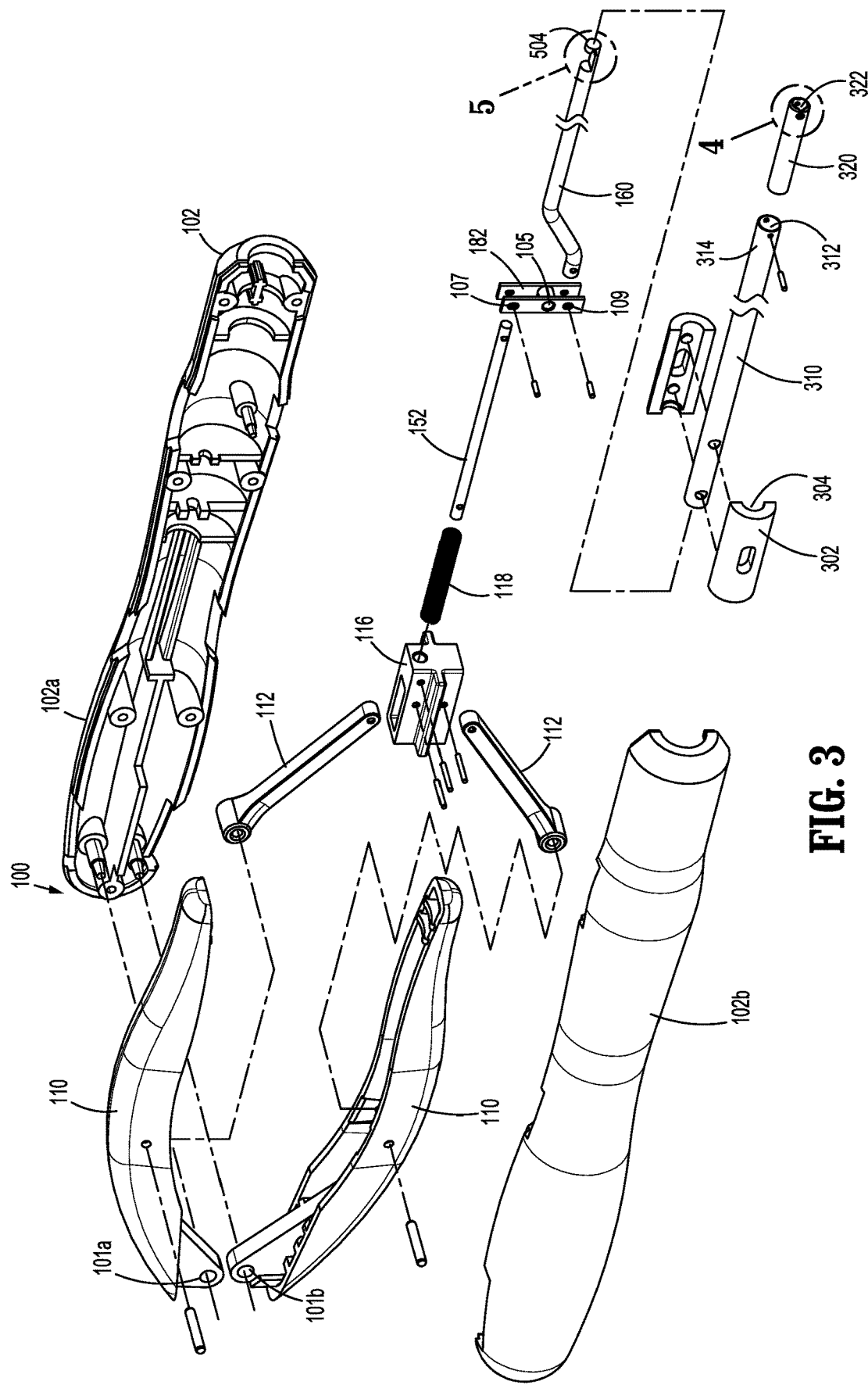
FIG. 3 is an exploded perspective view of the handle assembly of FIG. 2 with parts separated.

FIGS. 2 and 3 illustrate the handle assembly 100 including a housing 102 having first and second housing halves 102$a$, 102$b$, a pair of handles 110 pivotably secured to the housing 102 about respective pivots 101$a$, 101$b$, and a coupling portion 116. The pair of handles 110 is operatively coupled to an axial rod 152 such that when the pair of handles 110 is squeezed, the axial rod 152 is displaced distally. The pair of handles 110 is pivotably coupled to linkages 112 that are pivotably coupled to the coupling portion 116. The coupling portion 116 is coupled to the axial rod 152 to impart concomitant axial displacement to the axial rod 152. In particular, the axial rod 152 is biased proximally in the direction of an arrow "P" by a spring 118. Under such a configuration, the proximally biased axial rod 152 biases the coupling portion 116 towards a proximal-most position, which, in turn, places the pair of handles 110 in a spaced apart (i.e., unactuated) configuration. When the pair of handles 110 is squeezed by the clinician, the coupling portion 116 is displaced distally in the direction of an arrow "D", which imparts axial displacement to the axial rod 152 in the same direction.

The axial rod 152 is operatively coupled to the tool assembly 500 (FIG. 1) such that axial displacement of the axial rod 152 transitions the jaw 504 of the tool assembly 500 towards or away from the elongate shaft assembly 300 between the open and closed configurations, as will be discussed hereinafter.

FIGS. 2 and 3 further illustrate a lever 182 pivotably coupled to the housing 102 about a pivot 105. The axial rod 152 is pivotably coupled to the lever 182 about a pivot 107, and an actuation rod 160 is pivotably coupled to the lever 182 about a pivot 109. The pivots 107, 109 are laterally spaced apart on opposing sides of the lever 182 about the pivot 105. The actuation rod 160 is slidably supported through the elongate shaft assembly 300. Under such a configuration, axial displacement of the axial rod 152 pivots the lever 182, which, in turn, causes reciprocating displacement of the actuation rod 160 in an opposite direction.

Figure 4:
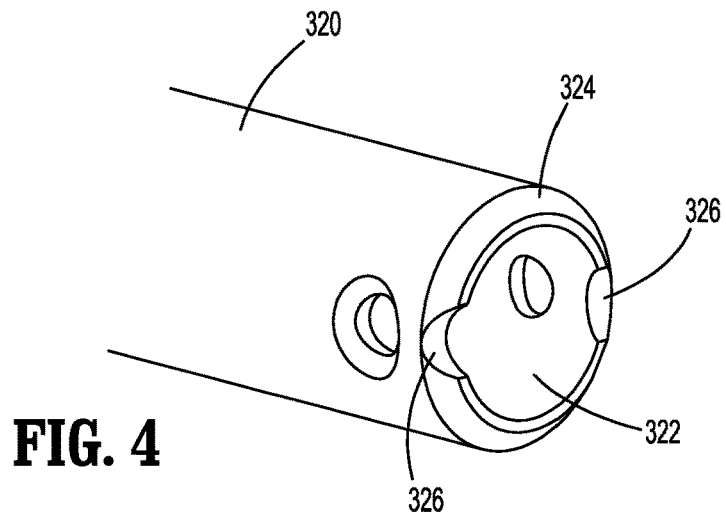
FIG. 4 is a perspective view of an inner tube of an elongate shaft assembly of the surgical stitching device of FIG. 1.

The elongate shaft assembly 300 incudes a sleeve 302 defining a lumen 304 therethrough, an outer tube 310, and an inner tube 320. The outer tube 310 extends through the lumen of the sleeve 302 and is secured to the sleeve 302. The sleeve 302 is secured to the housing 102. The outer tube 310 defines a lumen 312 therethrough. The lumen 312 is dimensioned to receive the actuation rod 160 therethrough. The inner tube 320 is disposed within the lumen 312 of the outer tube 310. In particular, the inner tube 320 is secured to a distal end portion 314 of the outer tube 310 such that at least a portion of the inner tube 320 extends distally from the outer tube 310. Further, FIG. 4 illustrates the inner tube 320 defining a lumen 322 to receive the actuation rod 160 therethrough. In addition, the inner tube 320 includes a lip 324 extending radially inward. The lip 324 may include a recessed portion 326 dimensioned to receive a portion of the suture needle 199 to facilitate securement of the suture needle 199 between the jaw 504 and the elongate shaft assembly 300, as will be discussed below. In particular, the lip 324 may include, e.g., diametrically opposing, recessed portions 326 to further facilitate securement of the suture needle 199 thereto.

Figure 5:
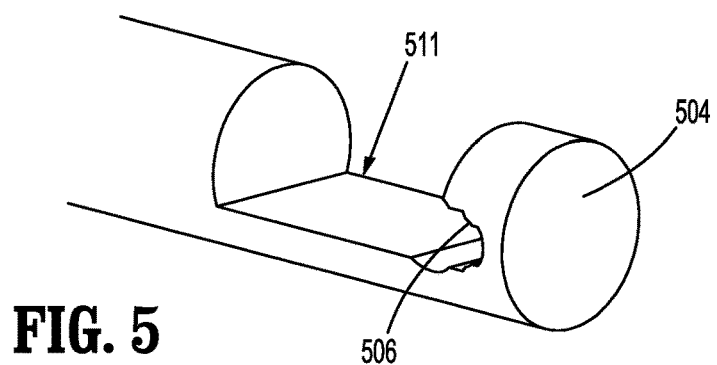
FIG. 5 is a perspective view of a jaw of a tool assembly of the surgical stitching device of FIG. 1.
Figure 6:
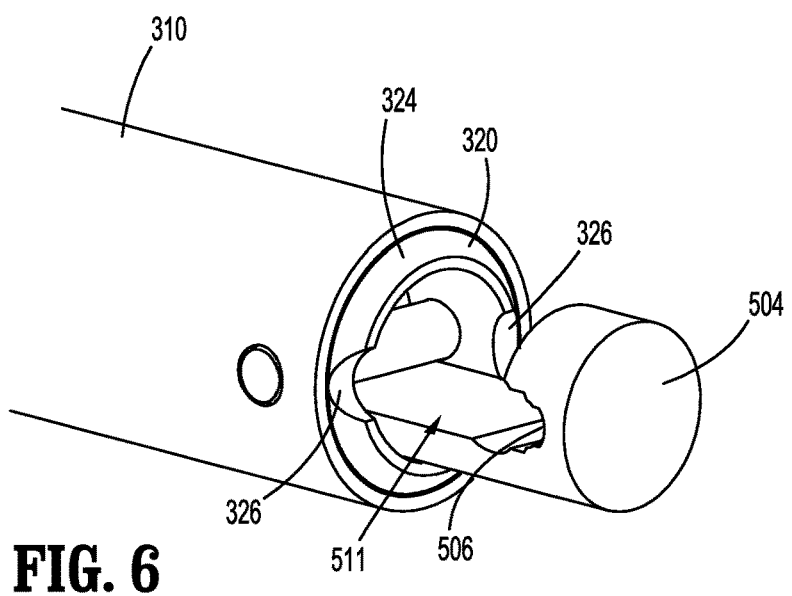
FIG. 6 is an enlarged perspective view of the indicated area of detail of FIG. 1.

FIGS. 5 and 6 illustrate the jaw 504 of the tool assembly 500. The jaw 504 is coupled to the actuation rod 160 (FIG. 3) and is dimensioned to extend through the lumen 322 (FIG. 4) of the inner tube 320. Under such a configuration, axial displacement of the actuation rod 160 imparts axial displacement to the jaw 504. In an aspect, the actuation rod 160 and the jaw 504 may be integrally formed as a single construct. In particular, the actuation rod 160 and the jaw 504 may be monolithically formed. The jaw 504 defines a cutout 511 thereby providing a hook profile to the jaw 504 to facilitate receipt of the suture needle 199 and securement of the suture needle 199 against the elongate shaft assembly 300, as will be discussed below. The jaw 504 further includes the recessed portion 506 in communication with the cutout 511. The recessed portion 506 is distal of the cutout 511.

Figure 7:
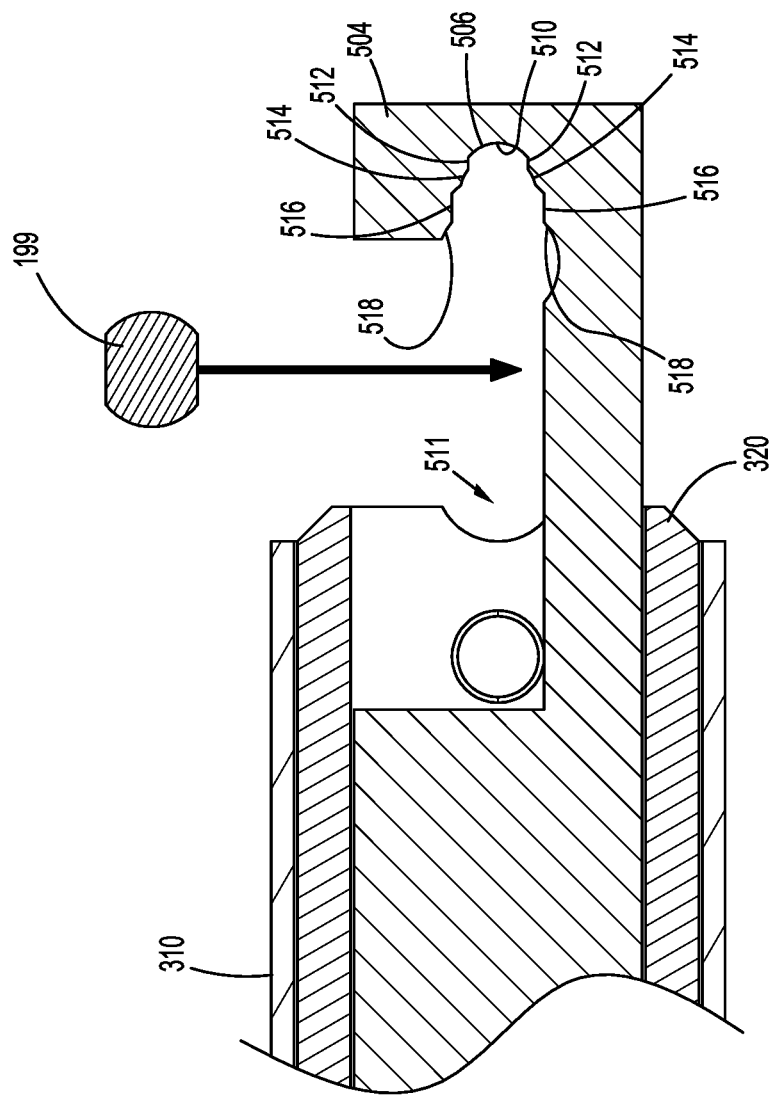
FIG. 7 is a partial, side cross-sectional view of the elongate shaft assembly and the tool assembly of the surgical stitching device of FIG. 1.
Figure 8:
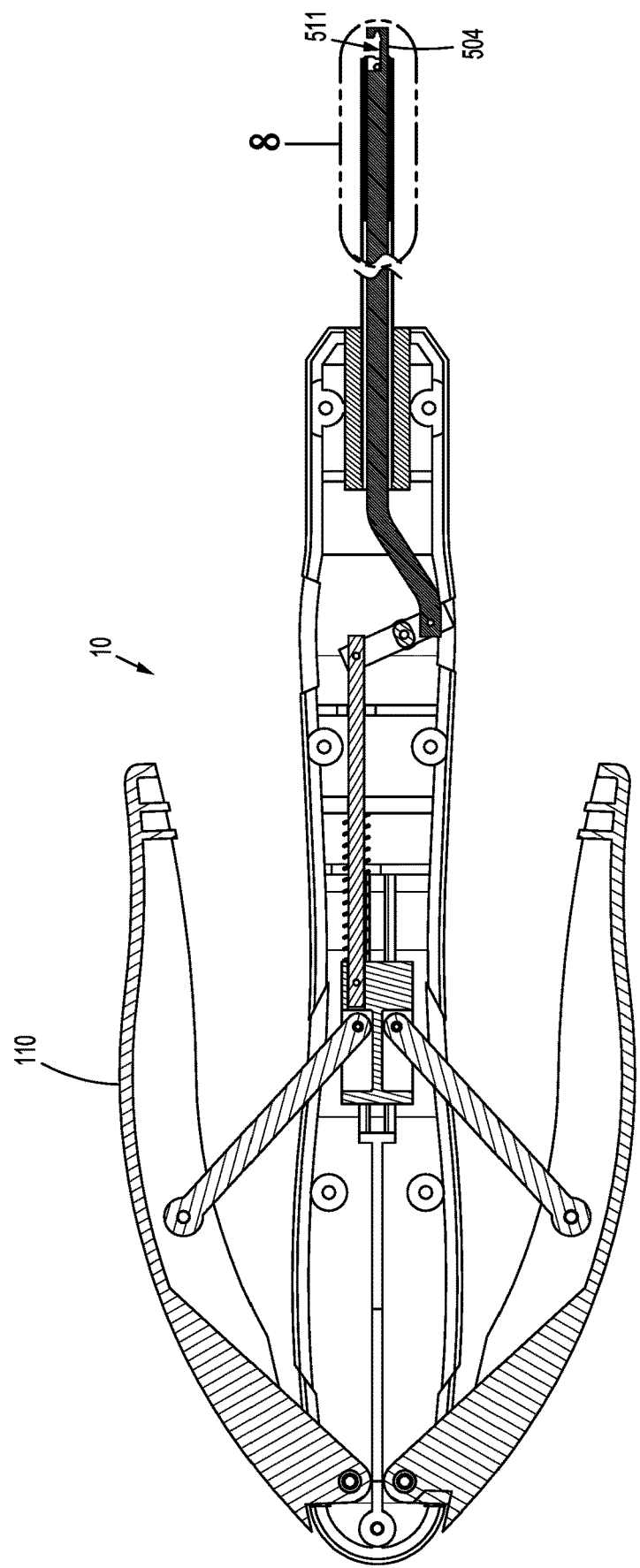
FIG. 8 is a side cross-sectional view of the surgical stitching device of FIG. 1 taken along section line 8-8 of FIG. 1.

FIGS. 7 and 8 illustrate the recessed portion 506 having a profile configured to receive various suture needles 199 in various orientations. The recessed portion 506 has a two-step configuration. In particular, the recessed portion 506 has a first arcuate surface 510 having a first radius of curvature, first opposing planar surfaces 512 distal of and coterminous with the first arcuate surface 510, second arcuate surfaces 514 proximal of and coterminous with the first opposing planar surfaces 512, second opposing planar surfaces 516 proximal of and coterminous with the respective second arcuate surfaces 514, and third arcuate surfaces 518 proximal of and coterminous with the respective second opposing planar surfaces 516. The second arcuate surfaces 514 have a second radius of curvature, and the third arcuate surfaces 518 have a third radius of curvature. The first, second, and third radii of curvature are different from each other. Under such a configuration, the tool assembly 500 may securely support the suture needle 199 in various orientations, as will be discussed. Further, such a configuration may enable use with various suture needles 199 having different dimensions, as will be discussed.

Figure 9:
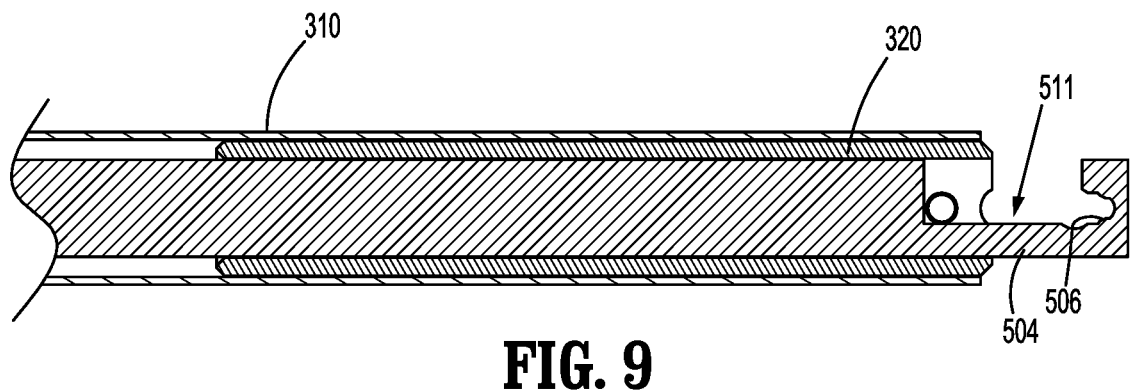
FIG. 9 is an enlarged cross-sectional view of the indicated area of detail of FIG. 8.
Figure 10:
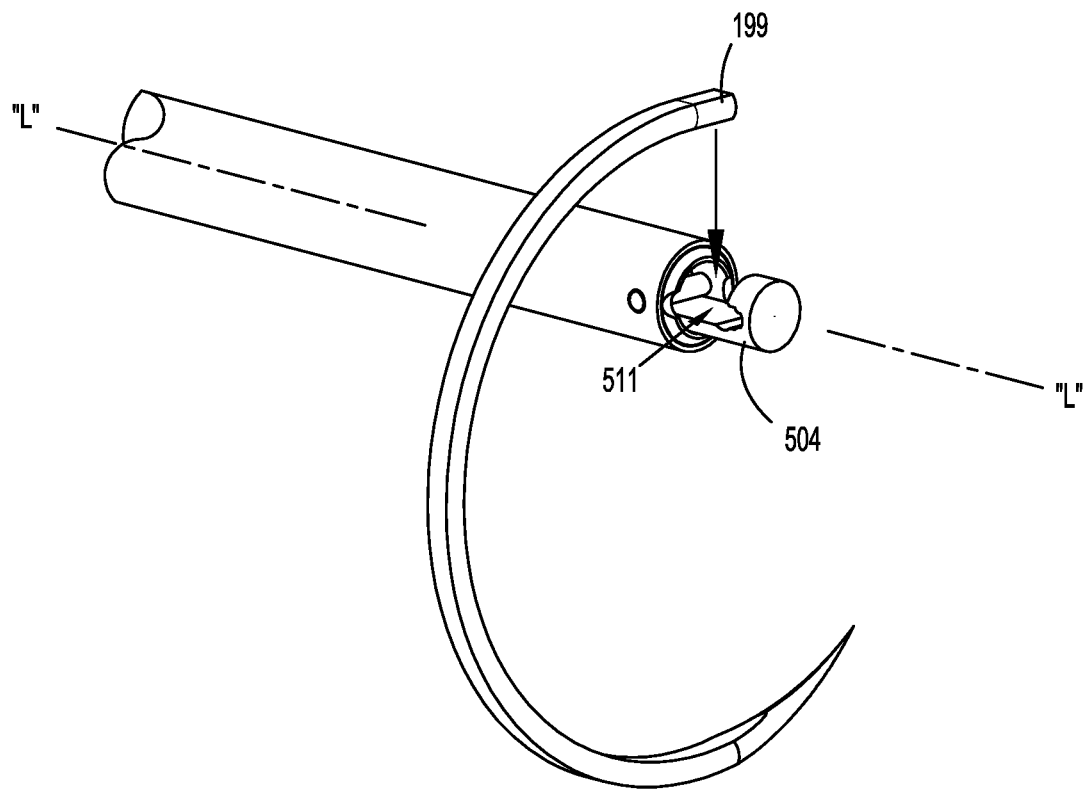
FIG. 10 is a partial perspective view of the elongate shaft assembly and the tool assembly of the surgical stitching device of FIG. 1, illustrating use with a suture needle of FIG. 1.

FIG. 9 illustrates the surgical stitching device 10 in an open configuration in which, the pair of handles 110 is in a spaced part configuration and the cutout 511 of the jaw 504 is exposed to receive the suture needle 199 (FIG. 10). The suture needle 199 is placed in the cutout 511 of the jaw 504 such that the suture needle 199 is, e.g., orthogonal, to a longitudinal axis "L-L" defined by the elongate shaft assembly 300.

Figure 11:
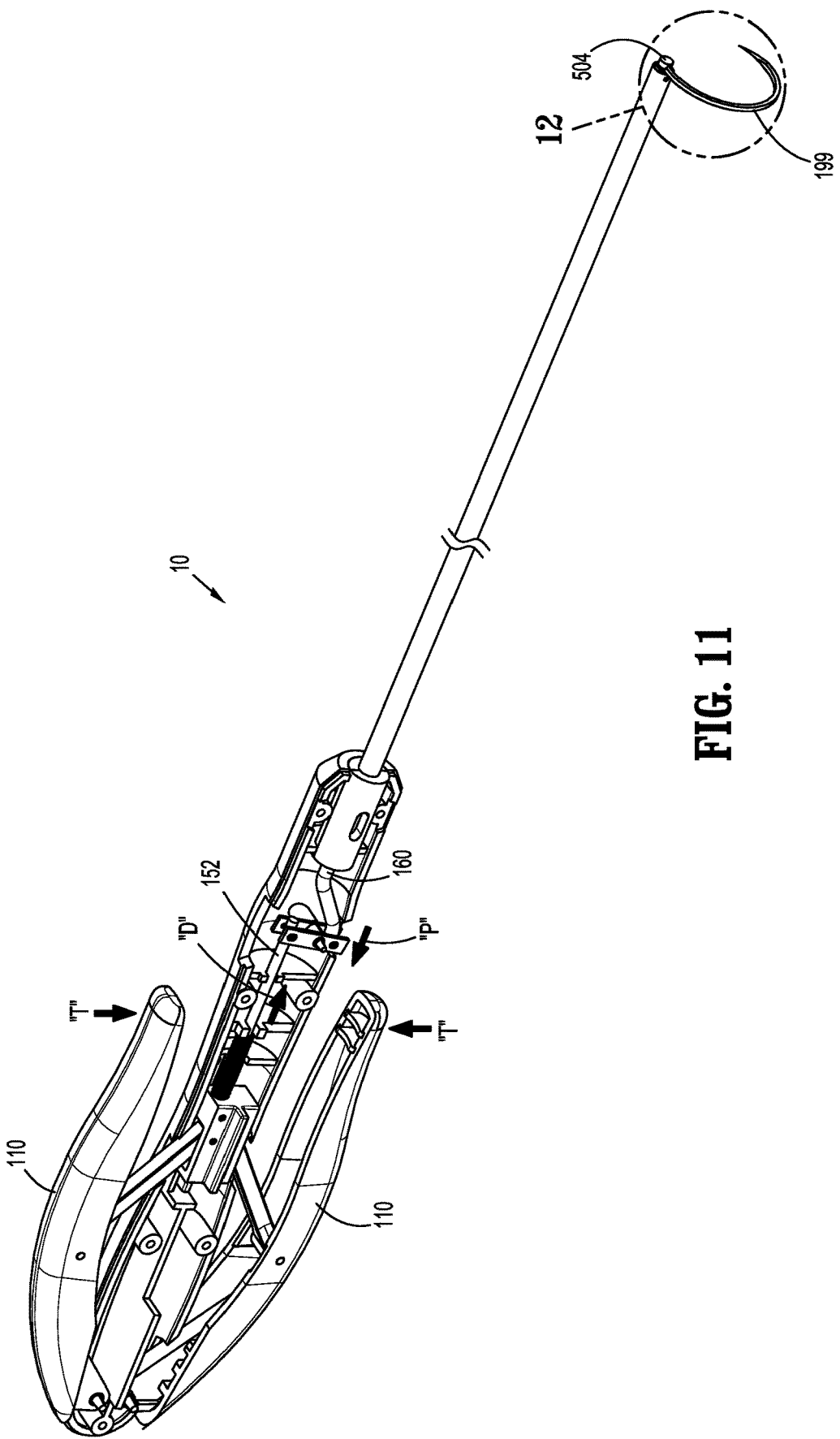
FIG. 11 is a perspective view of the surgical stitching device of FIG. 1 with a housing half removed, illustrating actuation of the handle assembly.

FIG. 11 illustrates the pair of handles 110 being squeezed by the clinician to grasp the suture needle 199 by the jaw 504 of the tool assembly 500. As the pair of handles 110 is squeeze in the direction of arrows "T", the axial rod 152 is displaced distally in the direction of an arrow "D". At this time, the actuation rod 160 is displaced proximally in the direction of an arrow "P" such that the suture needle 199 positioned within the recessed portion 506 and/or the cutout 511 is secured against the inner tube 320.

Figure 12:
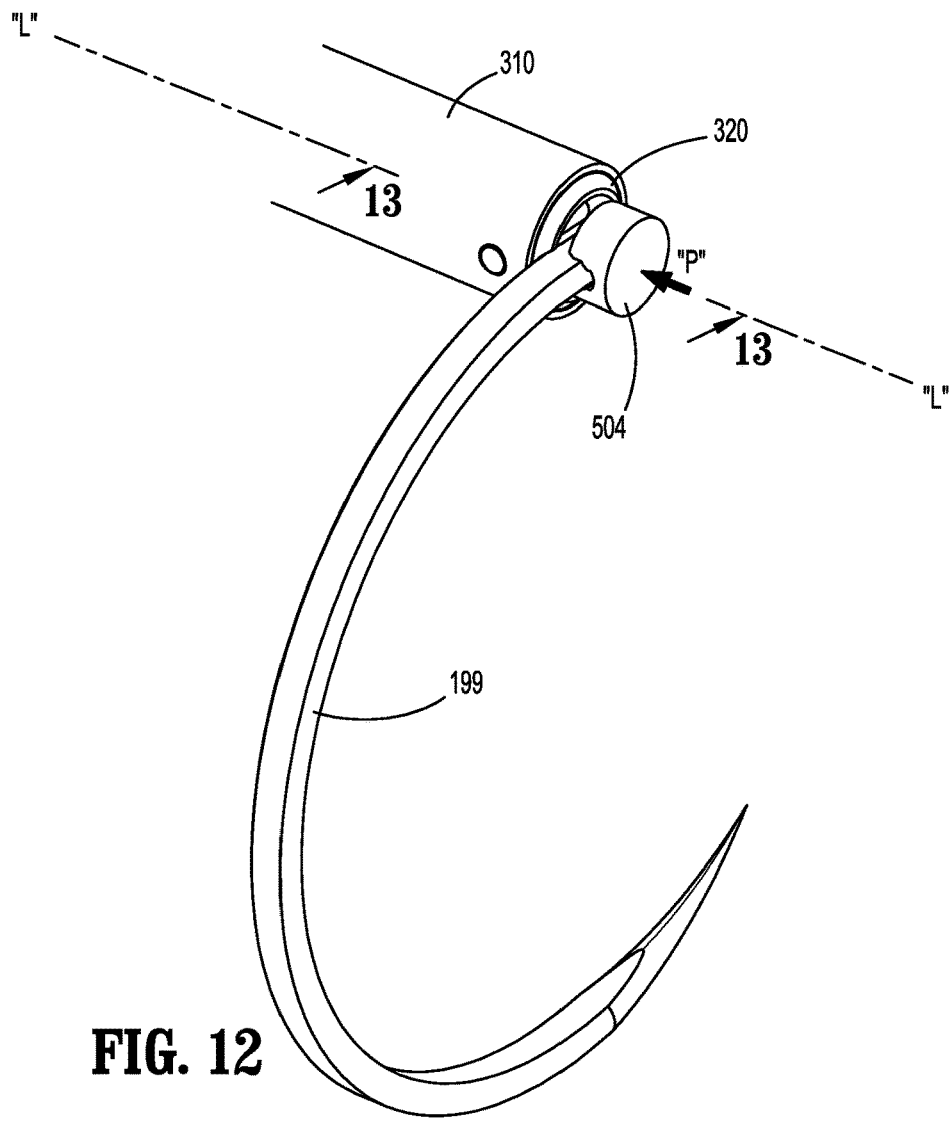
FIG. 12 is an enlarged perspective view of the indicated area of detail of FIG. 11.
Figure 13:
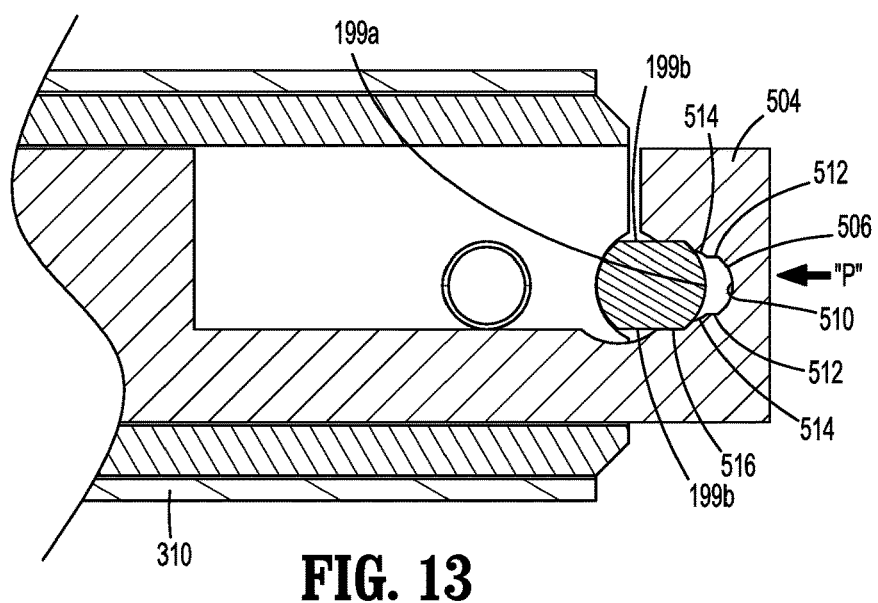
FIG. 13 is a side cross-sectional view of the elongate shaft assembly and the tool assembly of FIG. 12 taken along section line 13-13 of FIG. 12.

FIGS. 12 and 13 illustrate the suture needle 199 secured to the tool assembly 500. In particular, the suture needle 199 is disposed orthogonal to the elongate shaft assembly 300, i.e., an arcuate profile of the suture needle 199 is orthogonal to the longitudinal axis "L-L" defined by the elongate shaft assembly 300. When the suture needle 199 is supported against the elongate shaft assembly 300 in this manner, an arcuate portion 199a of the suture needle 199 engages the second arcuate surfaces 514 of the recessed portion 506 of the jaw 504, and the opposing planar surfaces 199b of the suture needle 199 engage the second opposing planar surfaces 516 of the recessed portion 506 of the jaw 504. In this manner, when the jaw 504 is retracted in the direction of an arrow "P" (FIG. 12), the suture needle 199 is fixed between the recessed portions 326 of the inner tube 320 and the recessed portion 506 of the jaw 504. In this manner, the suture needle 199 is non-rotatably fixed to facilitate suturing by the clinician.

Figure 14:
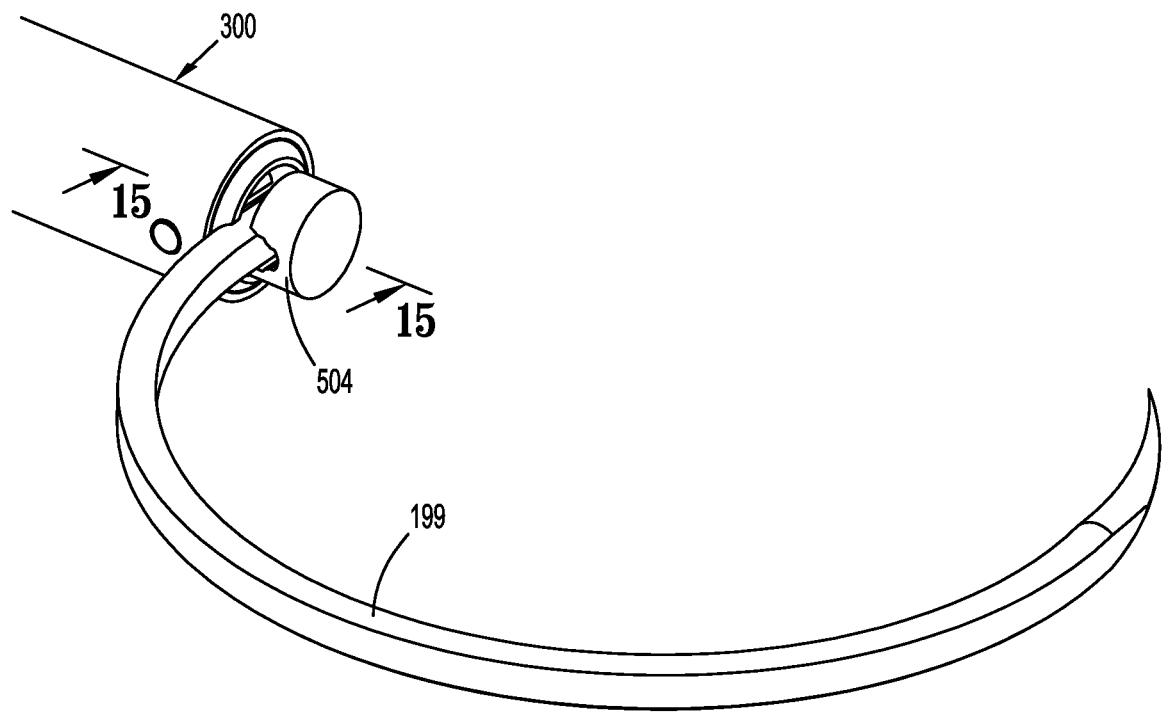
FIG. 14 is a partial perspective view of the elongate shaft assembly and the jaw of FIG. 12, illustrating use with the suture needle of FIG. 12 in a second orientation.
Figure 15:
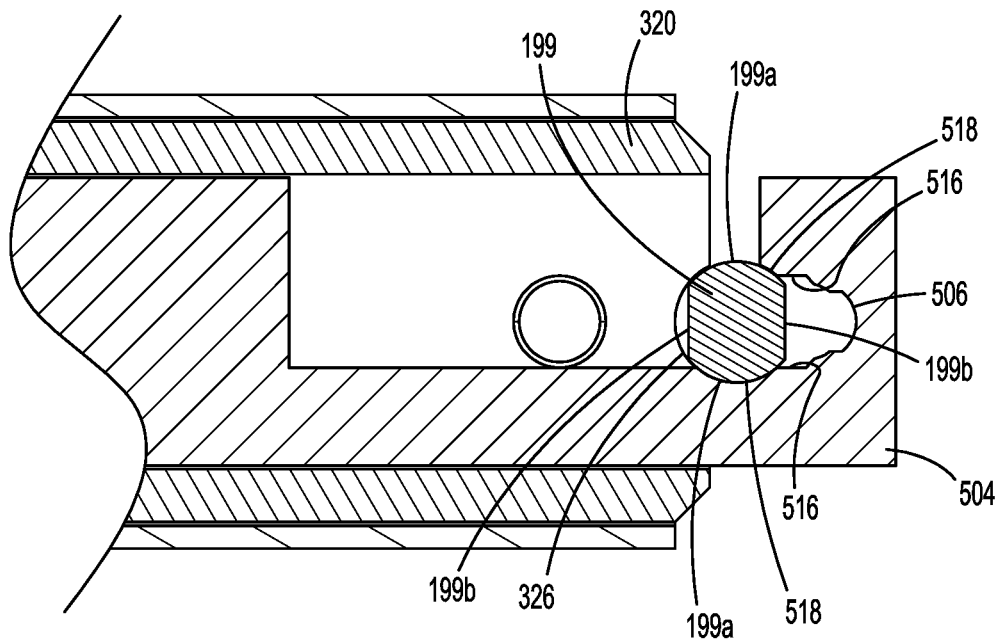
FIG. 15 is a side cross-sectional view of the elongate shaft assembly and the jaw of FIG. 14 taken along section line 15-15 of FIG. 14.

FIGS. 14 and 15 illustrate the suture needle 199 secured to the tool assembly 500 in a second orientation. In particular, the suture needle 199 is disposed on the longitudinal axis "L-L" of the elongate shaft assembly 300, i.e., a plane defined by the arcuate profile of the suture needle 199 is on the longitudinal axis "L-L." When the suture needle 199 is supported against the elongate shaft assembly 300 in this manner, the arcuate portions 199a of the suture needle 199 engage the third arcuate surfaces 518 of the recessed portion 506 of the jaw 504 and the recessed portions 326 of the inner tube 320. Further, a planar surface 199b of the suture needle 199 is received in the recessed portions 326 of the inner tube 320 and the opposing planar surface 199b is disposed between the second opposing planar surfaces 516 of the recessed portion 506 of the jaw 504. In this manner, when the jaw 504 is retracted in the proximal direction, the suture needle 199 is secured between the inner tube 320 and the jaw 504. In this manner, the suture needle 199 is non-rotatably fixed to facilitate suturing by the clinician.

Figure 16:
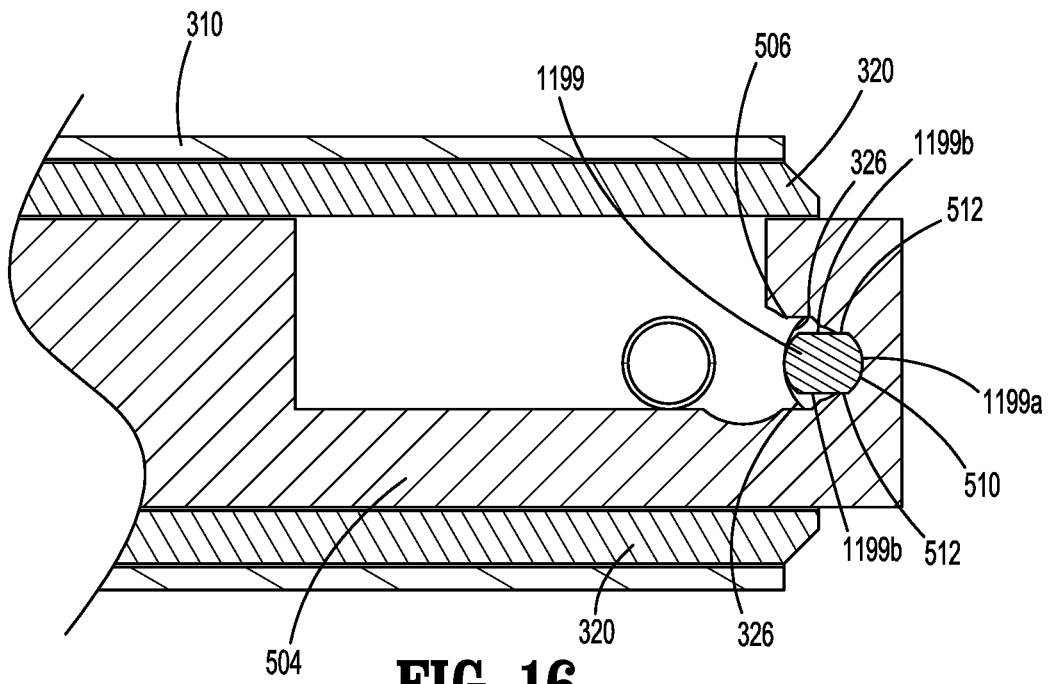
FIG. 16 is a partial side cross-sectional view of the elongate shaft and the jaw of FIG. 15 illustrating use with a second suture needle having smaller dimensions than the dimensions of the suture needle of FIG. 14.

FIG. 16 illustrates securement of a suture needle 1199 between the jaw 504 and the inner tube 320. The suture needle 1199 has smaller dimensions than the dimensions of the suture needle 199. When the suture needle 1199 is oriented in a manner similar to the suture needle 199 in FIG. 12, i.e., the suture needle 1199 is disposed orthogonal to the elongate shaft assembly 300, arcuate portions 1199a of the suture needle 1199 engage the first arcuate surface 510 of the recessed portion 506 of the jaw 504 and the recessed portions 326 of the inner tube 320. In addition, opposing planar surfaces 1199b of the suture needle 1199 engage the respective first opposing planar surfaces 512 of the recessed portion 506 of the jaw 504. In this manner, when the jaw 504 is retracted, the suture needle 1199 is secured between the inner tube 320 of the elongate shaft 300 and the jaw 504 such that the suture needle 1199 is non-rotatably fixed to facilitate suturing by the clinician.

Figure 17:
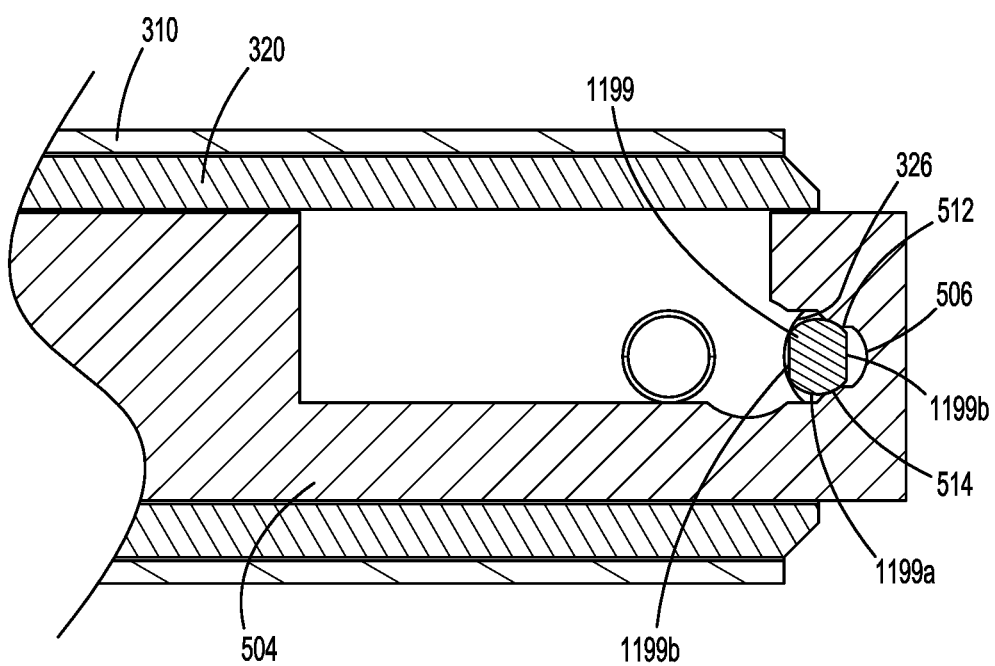
FIG. 17 is a partial side cross-sectional view of the elongate shaft assembly and the tool assembly of FIG. 16, illustrating use with the second suture needle of FIG. 16 in a second orientation.

FIG. 17 illustrates the securement of the suture needle 1199 between the jaw 504 and the inner tube 320 in a second orientation similar to the orientation of the suture needle 199 in FIG. 14. In particular, when the suture needle 1199 is oriented in such a manner, the arcuate portions 1199a of the suture needle 1199 engage the second arcuate surfaces 514 of the jaw 504 and the recessed portions 326 of the inner tube 320 of the elongate shaft assembly 300. In addition, one of the opposing planar surfaces 1199b of the suture needle 1199 engages the recessed portions 326 and the other one of the opposing planar surfaces 1199b is disposed between the first opposing planar surfaces 512 of the jaw 504. In this manner, when the jaw 504 is retracted, the suture needle 1199 is secured between the inner tube 320 of the elongate shaft 300 and the jaw 504 such that the suture needle 1199 is non-rotatably fixed to facilitate suturing by the clinician.

In use, the pair of handles 110 is initially squeezed to place the surgical stitching device 10 in the closed configuration, in which, the jaw 504 is retracted. At this time, the clinician may position the jaw 504 through an opening in tissue. Thereafter, the pair of handles 110 is released to transition the jaw 504 to the open configuration such that the jaw 504 is spaced apart from the elongate shaft assembly 300 to expose the cutout 511. While the jaw 504 is in the open configuration, the suture needle 199 or 1199 may be placed in the cutout 511 or the recessed portion 506 of the jaw 504. The pair of handles 110 is then squeezed to retract the jaw 504 to the closed configuration. At this time, the suture needle 199 or 1199 engages the recessed portion 506 of the jaw 504 and the recessed portions 326 of the inner tube 320 in a desired orientation. For example, the suture needle 199 or 1199 may be positioned to transversely extend around the jaw 504. With the suture needle 199 or 1199 secured with the jaw 504, the clinician may rotate the handle assembly 100 to draw the suture through the target tissue, thereby suturing the target tissue as needed or desired. The clinician may maneuver the surgical stitching device 10 as it is configured for a single hand operation. Specifically, the clinician may rotate the surgical stitching device 10 in the direction of the penetrating end portion 199p of the suture needle 199 such that the penetrating end portion 199p penetrates through tissue until the penetrating end portion 199p is exposed. In this manner, the suture needle 199 or 1199 may reliably pass through tissue present along, e.g., the edge of midline hernias. During the surgery, the clinician may switch to a different suture needle 199 or 1199 as needed without changing the surgical stitching device 10, thereby reducing the time of surgery and trauma to the patient. It is also contemplated that the surgical stitching device 10 may be used in conjunction with a mesh or other implants in the body.

It is envisioned that the surgical stitching device 10 may be configured to connect to a robotic arm of a robotic surgical system to enable manipulation and control thereof. It is also contemplated that the handle assembly 100 (FIG. 1) may be a powered or electromechanical handle assembly. It is to be understood, therefore, various other changes and modifications may be effected therein by one skilled in the art without departing from the scope or spirit of the disclosure.

While the disclosure has been shown in the drawings, it is not intended that the disclosure be limited thereto, as it is intended that the disclosure be as broad in scope as the art will allow and that the specification be read likewise. Therefore, the above description should not be construed as limiting, but merely as exemplifications. Those skilled in the art will envision other modifications within the scope and spirit of the claims appended hereto.

What is claimed is:

1. A surgical stitching device comprising:
an arcuate suture needle;
a handle assembly including a housing, a pair of handles, and an axial rod slidably supported in the housing, the axial rod operatively coupled to the pair of handles such that actuation of the pair of handles cause axial displacement of the axial rod;
an elongate shaft assembly extending distally from the handle assembly, the elongate shaft assembly including an actuation rod operatively coupled to the axial rod for reciprocating displacement in an opposite direction, and an outer tube defining a lumen therethrough, the actuation rod slidably disposed in the lumen of the outer tube; and
a tool assembly including a jaw coupled to the actuation rod, the jaw including a recessed portion configured to engage a portion of the arcuate suture needle, the jaw being axially transitionable between a retracted configuration, in which, the recessed portion is in a proximal position to clamp the arcuate suture needle against the elongate shaft assembly and an advanced configuration, in which, the recessed portion is spaced apart from the elongate shaft assembly, the recessed portion has a first arcuate surface, a first planar surface proximal of the first arcuate surface, a second arcuate surface proximal of the first planar surface, and a second planar surface proximal of the second arcuate surface, wherein the first arcuate surface has a first radius of curvature and the second arcuate surface has a second radius of curvature different from the first radius of curvature.

2. The surgical stitching device according to claim 1, wherein the arcuate suture needle has an arcuate portion having a radius of curvature identical to the first radius of curvature of the first arcuate surface of the recessed portion of the jaw.

3. The surgical stitching device according to claim 2, wherein the elongate shaft assembly further includes an inner tube secured to a distal end portion of the outer tube, the inner tube defines a second lumen dimensioned to slidably receive the actuation rod therethrough.

4. The surgical stitching device according to claim 3, wherein the inner tube further includes a lip extending radially inward.

5. The surgical stitching device according to claim 4, wherein the lip has a recessed portion configured to engage the portion of the arcuate suture needle.

6. The surgical stitching device according to claim 5, wherein the recessed portion of the lip has a radius of curvature identical to the radius of curvature of the arcuate portion of the arcuate suture needle.

7. The surgical stitching device according to claim 1, wherein an arcuate portion of the arcuate suture needle has a radius of curvature identical to the second radius of curvature of the second arcuate surface of the recessed portion of the jaw.

8. The surgical stitching device according to claim 1, wherein the first planar surface is coterminous with the first arcuate surface of the recessed portion of the jaw.

9. The surgical stitching device according to claim 1, wherein the second planar surface is coterminous with the second arcuate surface of the recessed portion of the jaw.

10. The surgical stitching device according to claim 1, wherein the recessed portion of the jaw further includes a third arcuate portion proximal of the second planar surface.

11. The surgical stitching device according to claim 10, wherein the third arcuate portion of the recessed portion of the jaw has a third radius of curvature different from the first or the second radii of curvature.

12. The surgical stitching device according to claim 10, wherein the third arcuate portion is coterminous with the second planar surface of the recessed portion of the jaw.

13. The surgical stitching device according to claim 1, wherein the arcuate suture needle has a penetrating end portion and a blunt end portion.

14. The surgical stitching device according to claim 1, wherein the jaw defines a cutout in communication with the recessed portion, the cutout configured to receive the portion of the arcuate suture needle.

15. A surgical stitching device comprising:
an elongate shaft assembly including a tube having a lip extending radially inward; and
a jaw being axially movable relative to the tube to clamp an arcuate suture needle between the tube and the jaw, the jaw including a recessed portion including:
a first arcuate surface;
a first planar surface proximal of the first arcuate surface;
a second arcuate surface proximal of the first planar surface; and
a second planar surface proximal of the second arcuate surface,
wherein the first arcuate surface has a first radius of curvature and the second arcuate surface has a second radius of curvature different from the first radius of curvature and the lip of the tube defines a recess having a radius of curvature identical to the second radius of curvature of the second arcuate surface of the recessed portion of the jaw.

16. The surgical stitching device according to claim 15, wherein the recessed portion of the jaw further includes a third arcuate surface proximal of the second planar surface.

17. The surgical stitching device according to claim 15, wherein the first planar surface is coterminous with the first arcuate surface and the second arcuate surface.

18. The surgical stitching device according to claim 15, further including a suture needle having a blunt end portion and a penetrating portion that diametrically oppose each other.

19. The surgical stitching device according to claim 18, wherein the jaw further defines a cutout configured to receive a portion of the suture needle, the cutout in communication with the recessed portion of the jaw.

\* \* \* \* \*